United States Patent
Williams et al.

(10) Patent No.: US 8,382,664 B2
(45) Date of Patent: Feb. 26, 2013

(54) MOLDED AND UNDIVIDED MEDICAL PENETRATING DEVICE

(75) Inventors: Derek M. Williams, Cuyahoga Falls, OH (US); George J. Picha, Brecksville, OH (US)

(73) Assignee: Applied Medical Technology, Inc., Brecksville, OH (US)

( * ) Notice: Subject to any disclaimer, the term of this patent is extended or adjusted under 35 U.S.C. 154(b) by 0 days.

(21) Appl. No.: 13/282,741

(22) Filed: Oct. 27, 2011

(65) Prior Publication Data

US 2012/0041270 A1 Feb. 16, 2012

Related U.S. Application Data

(63) Continuation-in-part of application No. 11/770,922, filed on Jun. 29, 2007, now Pat. No. 8,047,986.

(51) Int. Cl.
*A61B 1/00* (2006.01)
(52) U.S. Cl. ...................................................... 600/184
(58) Field of Classification Search .................. 600/184; 604/93.01, 104, 174, 175
See application file for complete search history.

(56) References Cited

U.S. PATENT DOCUMENTS

| | | | | |
|---|---|---|---|---|
| 3,788,327 | A * | 1/1974 | Donowitz et al. | 604/247 |
| 3,818,511 | A | 6/1974 | Goldberg et al. | |
| 3,882,862 | A * | 5/1975 | Berend | 604/8 |
| 5,087,244 | A | 2/1992 | Wolinsky et al. | |
| 5,308,325 | A * | 5/1994 | Quinn et al. | 604/96.01 |
| 5,356,391 | A * | 10/1994 | Stewart | 604/175 |
| 5,391,159 | A | 2/1995 | Hirsch et al. | |
| 5,439,444 | A * | 8/1995 | Andersen et al. | 604/102.02 |
| 5,458,573 | A | 10/1995 | Summers | |
| 5,464,395 | A | 11/1995 | Faxon et al. | |
| 5,476,434 | A * | 12/1995 | Kalb et al. | 600/30 |
| 5,688,237 | A * | 11/1997 | Rozga et al. | 604/500 |

(Continued)

FOREIGN PATENT DOCUMENTS

WO 95/18640 A1 7/1995

OTHER PUBLICATIONS

International Search Report and Written Opinion of the International Searching Authority, issued Nov. 27, 2008 in PCT/US2008/068765 (the international application corresponding to U.S. Appl. No. 11/770,922).

(Continued)

*Primary Examiner* — Ryan Severson
*Assistant Examiner* — Jonathan W Miles
(74) *Attorney, Agent, or Firm* — Pearne & Gordon LLP

(57) ABSTRACT

A molded and undivided medical penetrating device comprises a first portion and a second substantially tubular portion having an outer surface, a proximal end and a distal end. The proximal end of the second substantially tubular portion of the device is joined to and is integral with the first portion of the device and is adapted to be maintained essentially outside a body while the first portion of the device is adapted to be retained within the interior of the body. The device includes an opening that extends through the first and second portions of the device and provides access to the interior of the body from outside the body. The opening and the outer surface of the substantially tubular second portion of the device define a wall that is thinner at the proximal end of the second portion than towards the distal end of the second portion.

10 Claims, 2 Drawing Sheets

U.S. PATENT DOCUMENTS

| | | | |
|---|---|---|---|
| 5,861,036 A * | 1/1999 | Godin | 623/23.64 |
| 5,941,855 A * | 8/1999 | Picha et al. | 604/174 |
| 6,186,985 B1 * | 2/2001 | Snow | 604/175 |
| 6,322,538 B1 * | 11/2001 | Elbert et al. | 604/174 |
| 6,364,858 B1 | 4/2002 | Picha | |
| 6,402,722 B1 * | 6/2002 | Snow et al. | 604/164.05 |
| 6,494,862 B1 | 12/2002 | Ray et al. | |
| 6,896,665 B2 | 5/2005 | Picha et al. | |
| 2008/0275306 A1 * | 11/2008 | Rebuffat et al. | 600/184 |

OTHER PUBLICATIONS

Supplementary Partial European Search Report issued Mar. 28, 2011 in European Patent Application No. 08772240.1 (the European application corresponding to U.S. Appl. No. 11/770,922).

Office action issued Jul. 20, 2011 in Canadian Patent Application Serial No. 2,691,633 (the Canadian application corresponding to U.S. Appl. No. 11/770,922).

\* cited by examiner

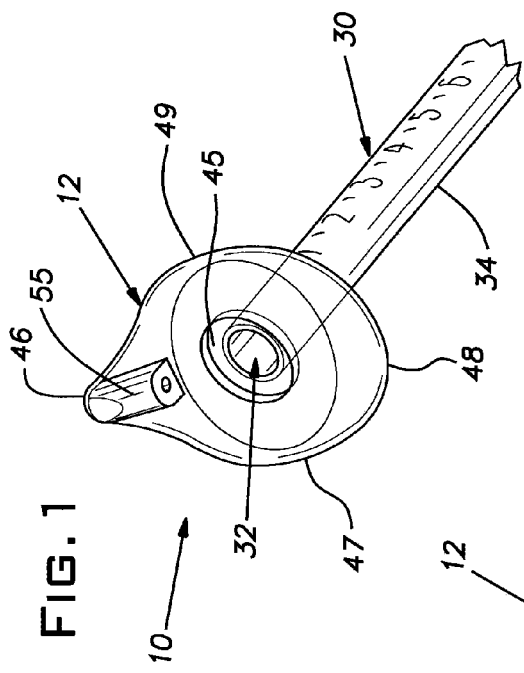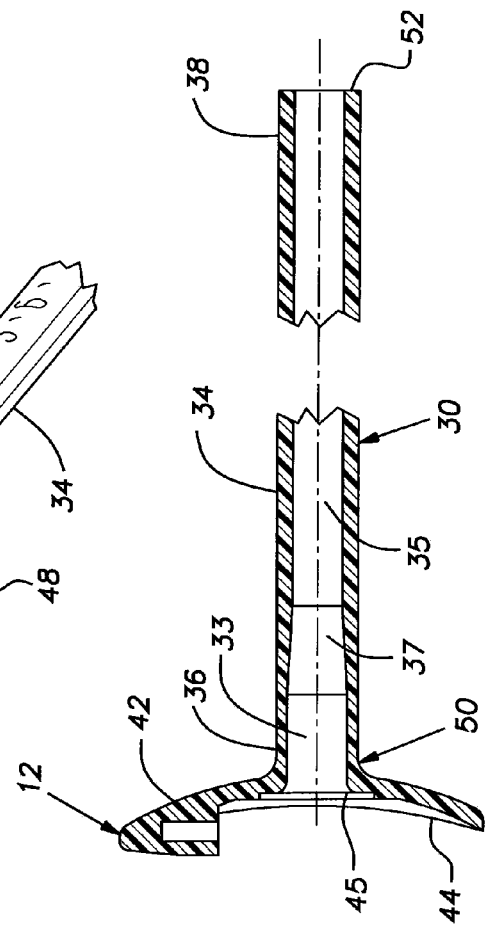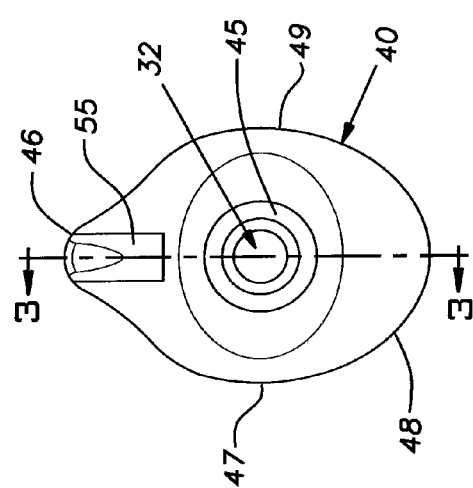

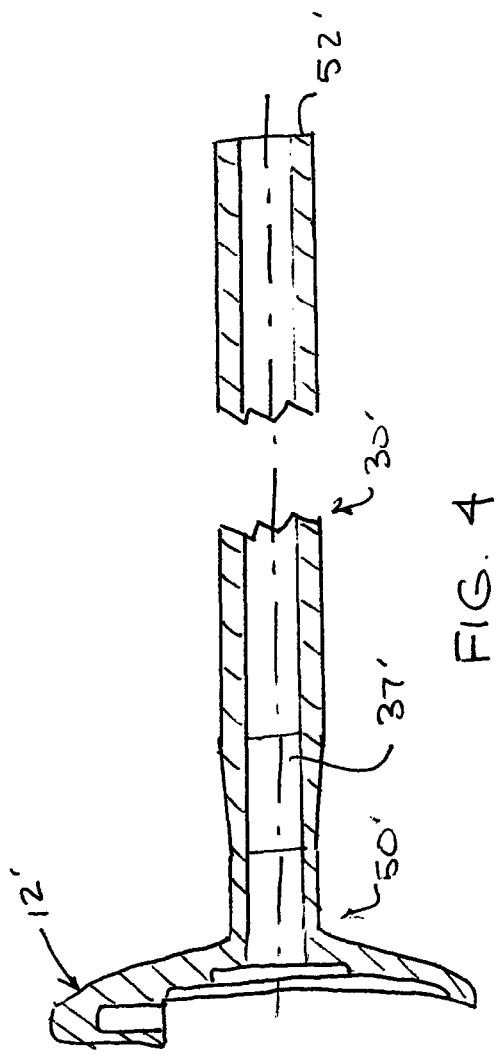
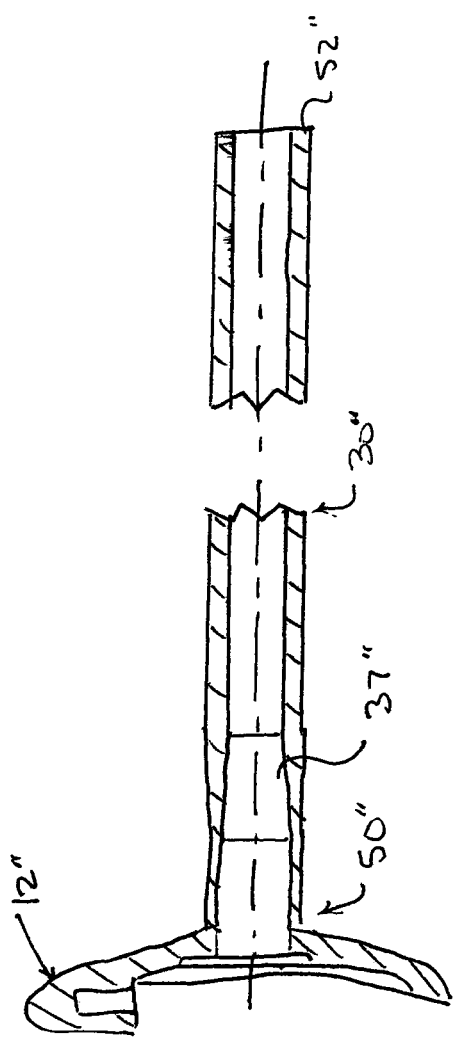

MOLDED AND UNDIVIDED MEDICAL PENETRATING DEVICE

BACKGROUND OF THE INVENTION

The present invention relates to medical penetrating devices and in particular to molded and undivided medical penetrating devices that are adapted for insertion into a body cavity.

Certain medical conditions require the use of medical penetrating devices that are adapted to be inserted into a body cavity through an opening in the body. Examples of medical procedures where such medical penetrating devices may be employed for providing access to body viscera include, for example, ileostomies, jejunostomies, cystostomies and other urological procedures such as procedures for draining a bladder for example. In particular, gastrostomy devices are designed to penetrate through an opening, typically made by an incision, in the wall of the abdomen into the stomach of a patient. The gastrostomy device thereby provides access to the patient's stomach from outside so that the patient can be furnished with necessary fluids such as nutrients and medications. Such medical penetrating devices also can be used for decompression of the gut and to provide a means of access in connection with various examining procedures such as endoscopic examinations for example.

BRIEF SUMMARY OF THE INVENTION

The following presents a simplified summary of the invention in order to provide a general understanding of certain aspects of the invention. The summary is not intended to comprise an extensive overview of the invention. Nor is the summary intended necessarily to identify critical elements of the invention or delineate the scope of the invention. The sole purpose of the summary is to present certain concepts of the invention in a simplified form as an introduction to the more detailed description of the invention that follows thereafter.

The present device is adapted to be employed in a variety of medical contexts or circumstances where the device is used to penetrate into the interior of a body through an opening in the body. The device is manufactured as an undivided, or unitary, structure employing a molding procedure.

In one aspect, a molded and undivided medical penetrating device that comprises a first portion and a second portion is provided. The first portion of the device is adapted for insertion into the interior of a body through an opening in the body and for retention within the body interior following insertion. A second portion of the device is integrally joined to the first portion of the device by a joining portion of the device and is adapted to be maintained essentially outside the body while the first portion of the device is retained in the body. The second portion of the device has a substantially tubular configuration and includes an outer surface, a proximal end that is adjacent to the first portion of the device and a distal end that is removed from the first portion of the device. An opening extends through the first and second portions of the device and provides access to the interior of the body from outside the body. The outer surface of the substantially tubular second portion of the device and the opening extending through the substantially tubular second portion of the device form a wall therebetween. The thickness of the wall at the location where the first portion of the device and the tubular second portion of the device are integrally joined to one another by the joining portion of the device is less than the thickness of the wall adjacent thereto but nearer the distal end of the substantially tubular second portion of the device. The joining portion of the device is sufficiently flexible to allow the first portion of the device to be folded at the joining portion against the outer surface of the substantially tubular second portion.

According to another aspect, the first portion of the molded and undivided medical penetrating device comprises two external surfaces that oppose one another. One of the external surfaces is substantially convex and is integrally joined to the outer surface of the substantially tubular second portion of the device by the joining portion of the device and the other of the external surfaces is substantially concave. A recess can be provided in the substantially concave external surface of the first portion of the device so that the recess extends in the direction of the substantially convex external surface of the first portion of the device and surrounds the opening where the opening extends through the first portion of the device. Additionally, the first portion of the device can be constructed so as to flare generally radially away from the substantially tubular second portion of the device. In that case, the first portion of the device has a margin that lies generally radially outwardly of the substantially tubular second portion of the device. Also, the generally concave external surface of the first portion of the device can include a salient portion adjacent the margin of the first portion of the device, whereby the salient portion may serve as a focal point for the folding of the first portion of the device onto itself.

In a further aspect, the opening that extends through the substantially tubular second portion of the molded and undivided medical penetrating device can include a first length that is located at the joining portion of the device and has a first cross-sectional area. A second length of the opening can be located nearer the distal end of the substantially tubular second portion of the device than the first length and have a second cross-sectional area that is less than the first cross-sectional area. A transitional length of the opening can join the first length and the second length in that case.

According to a further aspect, the first portion of the molded and undivided medical penetrating device is larger than the opening in the body through which the first portion of the device is adapted to be inserted. And the first portion of the device is adapted to seat against a surface at the interior of the body around the opening in the body whereby the first portion of the device may be retained within the body at the opening in the body.

The molded and undivided medical penetrating device can be made by providing a melt of a material from which the device is to be manufactured, injecting the melt into a mold cavity that has an appropriate configuration, allowing the melt to set in the mold cavity and removing the device from the mold cavity.

The molded and undivided medical penetrating device can be made of a silicone or a thermoplastic elastomer.

BRIEF DESCRIPTION OF THE DRAWINGS

FIG. 1 is a partial perspective view of an embodiment of a molded and undivided medical penetrating device according to the invention.

FIG. 2 is a top view of the embodiment of the invention shown in FIG. 1.

FIG. 3 is a cross-sectional view of the embodiment of the invention shown in FIG. 1 along line 3-3 of FIG. 2.

FIG. 4 is a cross-sectional view of another embodiment of the invention shown in FIG. 1 along line 3-3 of FIG. 2.

FIG. 5 is a cross-sectional view of yet another embodiment of the invention shown in FIG. 1 along line 3-3 of FIG. 2.

DETAILED DESCRIPTION OF AN EMBODIMENT OF THE INVENTION

Reference will now be had to the accompanying drawings in which is illustrated an embodiment of the invention referenced generally by the reference numeral 10. The invention comprises a molded and undivided medical penetrating device. That is, the device can be used in medical contexts or circumstances involving tube-accessible applications. Examples of such applications are gastrostomies, ileostomies, jejunostomies, cystostomies and other urological procedures as well as various thoracic procedures and procedures for draining wounds and infections; the device can be used to penetrate within the interior of the body through an opening in a body whereby access can be had to the interior of the body from outside the body; and the device can be formed as an undivided, unitary or one-piece structure in a molding process. The embodiment of the invention illustrated in the drawings comprises a first portion of the molded and undivided medical penetrating device, indicated generally at 12, and a second portion of the device, indicated generally at 30. The first portion of the device is adapted for insertion into the interior of a body through an opening in the body. For example, when the device is used in connection with the performance of a gastrostomy, an incision would be made through the wall of the abdomen into the stomach and the first portion 12 of the device would be inserted into the stomach through the incision. Typically, the first portion 12 of the device would be folded in a manner that would minimize the space that it occupies and allow the first portion of the device to be inserted into the stomach through a smaller incision than would otherwise be required. This is accomplished in a manner that will be familiar to those having ordinary skill in the art and is not described in detail here except to note that the first portion 12 of the device, after it is folded, can be inserted into a tubular-like delivery capsule that keeps the first portion 12 from unfolding. The capsule is then used to insert the first portion 12 of the device into the body after which the first portion is released from the capsule and assumes its unfolded state. Selected techniques that could be adapted to inserting the device disclosed herein are disclosed in U.S. Pat. No. 6,896,665.

The first portion 12 of the device is also adapted for retention in the body following insertion. Thus, again in the case where the device 10 is used in connection with the performance of a gastrostomy, the first portion 12 of the device, after it is inserted into the stomach and unfolds as described in the previous paragraph, returns to the shape it normally has as shown in the drawings. At that time, the second portion 30 of the device 10 can be pulled in a direction away from the abdomen and the first portion 12 of the device brought into good contact and engagement with the wall of the stomach. It will be understood based on the foregoing description that the first portion 12 of the device 10 is larger than the opening in the body through which the first portion of the device is adapted to be inserted, and the first portion of the device is adapted to seat against a surface of the interior of the body around the opening in the body whereby the first portion 12 of the device 10 may be retained at the interior of the body at the opening in the body.

As indicated above, the molded and undivided medical penetrating device shown in the accompanying drawings also comprises a second portion 30 of the molded and undivided medical penetrating device 10 that is joined to and is integral with the first portion 12 of the device and is adapted to be maintained essentially outside the body while the first portion 12 of the device is retained within the body. The presence of the second portion 30 of the device outside the body provides a means for the introduction or withdrawal or drainage of fluids and the like into and from the body in which the first portion 12 of the device 10 is located. Thus, the device 10 includes an opening 32 that extends through the first portion 12 of the device and the second portion 30 of the device and provides access to the interior of the body from outside the body. Thereby, in the case of the use of the device illustrated in the drawings, in a gastrostomy, the second portion 30 of the device 10 can be connected to apparatus for delivering nutrients to the stomach through the opening 32.

The description of the first portion 12 of the device 10 as being integral with the second portion 30 of the device is intended to mean that the first portion 12 and second portion 30 are unitary and of one-piece. Stated otherwise, the first and second portions are formed as an undivided structure. That is, the first portion 12 and the second portion 30 are not made as separate components that are subsequently joined together such as by the use of adhesives for example. In the embodiment shown in the drawings, a joining portion 50 of the device joins the first portion 12 of the device and the second portion 30 of the device.

In the illustrated embodiment, the second portion 30 of the molded and undivided medical penetrating device 10 has a substantially tubular configuration and includes an outer surface 34, a proximal end 36 adjacent to the first portion 12 of the device 10 and a distal end 38. The first portion 12 of the molded and undivided medical penetrating device 10 flares generally radially away from the substantially tubular second portion 30 of the device so as to have a margin, indicated generally at 40, lying generally radially outwardly of the substantially tubular second portion 30 of the device 10. The first portion 12 of the device 10 comprises two external surfaces 42 and 44 that oppose one another. One of the external surfaces, external surface 42, is substantially convex and is integrally joined to the outer surface 34 of the substantially tubular second portion 30 of the device 10 at the joining portion 50 of the device. The other of the external surfaces, external surface 44, is substantially concave. A substantially circular recess 45 is located in the substantially concave external surface 44 of the first portion 12 of the device 10, and the recess 45 extends in the direction of the substantially convex external surface of the first portion of the device and surrounds the opening 32 where the opening extends through the first portion 12 of the device 10.

The margin 40 of the first portion 12 of the molded and undivided medical penetrating device 10 is generally elliptical in shape and includes a tapering end 46, a rearward end 48 located opposite the tapering end and two opposed elliptical sides 47 and 49 that connect respective termini of the ends 46 and 48.

The opening 32 that extends through the substantially tubular second portion 30 of the device 10 and the outer surface 34 of the substantially tubular second portion of the device form a wall 52 therebetween. The thickness of the wall 52 at the location where the first portion 12 of the device 10 and the tubular second portion 30 of the device 10 are integrally joined to one another by the joining portion 50 is less than the thickness of the wall adjacent thereto but nearer the distal end 38 of the tubular second portion 30 of the device 10. More specifically, the opening 32 that extends through the substantially tubular second portion 30 of the device 10 includes a first length 33 that is located at the integral jointure or joining portion 50 of the device and has a first cross-sectional area. The opening 32 also includes a second length 35 that is nearer the distal end 38 of the second portion 30 of the device than the first length 33 of opening and has a second cross-sectional area that is less than the first cross-sectional area of the first length 33 of the opening 32. A transitional length 37 of the opening 32 joins the first length 33 and the second length 35 of the opening 32. Turning now to FIGS. 4 and 5, a similar effect can be provided by reducing the outside diameter of the outer surface of the substantially tubular second portion of the device at the joining portion 50', as shown in FIG. 4; or by both reducing the outside diameter of the outer surface and increasing the diameter of the inner surface at the joining portion 50", as shown in FIG. 5. In each example, the tubular second portion of the device 30' and 30" are monolithically formed with the first portion 12' and 12" of the device, respectively.

Typically, the molded and undivided medical penetrating device of the invention is made of a biocompatible, long-lasting and resiliently deformable material. The device normally is made to be biocompatible so that it will not be rejected by or create other complications with the patient. The device is usually long-lasting, particularly in those instances in which the device will remain in the patient for an extended period of time. The device is also resiliently deformable so that it can be easily manipulated for insertion into the interior of a body and to facilitate the handling of other stresses that may be applied to the device. The device can be made of a silicone or a thermoplastic elastomer that satisfies these requirements.

Achieving the requirement that the device be readily deformable is also made possible by the structural features of the device as related above. Thus, the narrowing of the wall 52 of the substantially tubular second portion 30 of the device 10 at the joining portion 50 as a result of the enlarging of the opening 32 at the location 33 and the location of the recess 45 nearby, thereby providing in the latter case for the absence of excessive construction material thereat, contribute to the deformability of the device. As a result, the joining portion 50 of the device 10, which is located where the first portion 12 of the device 10 and the substantially tubular second portion 30 of the device 10 are integrally joined to one another, is sufficiently flexible to allow the first portion 12 of the device to be folded at the joining portion 50 against the outer surface 34 of the substantially tubular second portion 30 of the device. Specifically, the rearward end 48 of the first portion 12 of the device can be folded at the joining portion 50 downwardly as viewed in FIG. 1 and into contact with the outer surface 34 of the substantially tubular second portion 30 of the device.

The structural features of the device 10 referred to in the previous paragraph contribute not only to the ease of folding of the rearward end 48 of the first portion 12 of the device as described in the previous paragraph but also to the folding of the first portion 12 of the device onto itself along a fold line that runs between the tapering end 46 and the rearward end 48 of the first portion 12. In connection with this latter folding feature, the generally concave external surface 44 of the first portion 12 of the device 10 includes a salient portion 55, that extends above the generally concave external surface 44 of the first portion 12 of the device, adjacent the margin 40 and at the tapering end 46 of the first portion 12 of the device 10. Thereby, the salient portion may serve as a focal point for the folding of the first portion 12 of the device 10 onto itself along a fold line that extends between the tapering end 46 and the rearward end 48 of the first portion 12 of the device 10. The folding of the first portion 12 of the device 10 in the two respects described together with the upturning of the tapering end 46 facilitates the insertion of the first portion of the device into a delivery capsule as referenced above. The molded and undivided medical penetrating device of the invention can then be inserted into the interior of a body such as through a gastrostomy opening.

Reference has been made to the fact that molded and undivided medical penetrating device of the invention is comprised of a unitary, one-piece construction. Such a construction can be accommodated by providing a melt of a material, such as a silicone or a thermoplastic elastomer for example, from which the device is to be manufactured; injecting the melt into a mold cavity that has a configuration conforming to the configuration of the molded and undivided medical penetrating device of the invention; allowing the melt to set in the mold cavity; and removing the device from the mold cavity.

Although the invention has been described with reference to specific embodiments, it will be understood that the invention can be practiced employing modifications and variations within the spirit and scope of the claims that follow.

What is claimed is:

1. A molded and undivided medical penetrating device comprising:
   a first portion of the device configured for insertion into an interior of a body through an opening in the body;
   a second portion of the device monolithically formed with the first portion of the device by a joining portion and configured to be maintained essentially outside the body while the first portion of the device is retained within the body, the second portion of the device having a substantially tubular configuration and including an outer surface, a proximal end adjacent the first portion of the device and a distal end; and
   an opening extending through the first portion of the device and the second portion of the device and providing access to the interior of the body from outside the body, the outer surface of the substantially tubular second portion of the device and the opening extending through the substantially tubular second portion of the device forming a substantially tubular wall therebetween, and a thickness of the substantially tubular wall at the location where the first portion of the device and the tubular second portion of the device are integrally joined to one another by the joining portion of the device being less than a thickness of the substantially tubular wall nearer the distal end,
   wherein an outer diameter of the substantially tubular second portion is decreased at the joining portion.

2. The molded and undivided medical penetrating device of claim 1 wherein, an inner diameter of the substantially tubular second portion is uniform at the joining portion.

3. The molded and undivided medical penetrating device of claim 1, wherein an inner diameter of the substantially tubular second portion is increased at the joining portion.

4. The molded and undivided medical penetrating device of claim 1 wherein:
   the first portion of the device comprises two external surfaces that oppose one another, one of the external surfaces being substantially convex and integrally joined to the outer surface of the substantially tubular second portion of the device by the joining portion of the device and the other of the external surfaces being substantially concave.

5. The molded and undivided medical penetrating device of claim 4 including:
   a recess in the substantially concave external surface of the first portion of the device extending in the direction of the substantially convex external surface of the first portion of the device and surrounding the opening where the opening extends through the first portion of the device.

6. The molded and undivided medical penetrating device of claim 1 wherein:
the joining portion of the device is sufficiently flexible to allow the first portion of the device to be folded at the joining portion against the outer surface of the substantially tubular second portion of the device.

7. The molded and undivided medical penetrating device of claim 1 wherein:
the opening that extends through the substantially tubular second portion of the device includes a first length that is located at the joining portion of the device and has a first cross-sectional area, a second length that is nearer the distal end of the substantially tubular second portion of the device than the first length and has a second cross-sectional area that is less than the first cross-sectional area of the first length, and a transitional length that joins the first length and the second length.

8. The molded and undivided medical penetrating device of claim 1 wherein:
the first portion of the device flares generally radially away from the substantially tubular second portion of the device so as to have a margin lying generally radially outwardly of the substantially tubular second portion of the device; and a generally concave external surface of the first portion of the device includes a salient portion adjacent the margin of the first portion of the device, whereby the salient portion may serve as a focal point for folding of the first portion of the device onto itself.

9. The molded and undivided medical penetrating device of claim 1 wherein:
the first portion of the device is larger than the opening in the body through which the first portion of the device is adapted to be inserted; and
the first portion of the device is adapted to seat against a surface of the interior of the body around the opening in the body, whereby the first portion of the device may be retained at the interior of the body at the opening in the body.

10. The molded and undivided medical penetrating device of claim 1 wherein the device is made of a silicone or a thermoplastic elastomer.

* * * * *